United States Patent [19]

Weber

[11] Patent Number: 4,927,259

[45] Date of Patent: May 22, 1990

[54] APPARATUS AND METHOD FOR TESTING VISUAL FIELD

[76] Inventor: Joerg Weber, Auf dem Muehlenacker 40, 5030 Huerth-Hermuelheim, Fed. Rep. of Germany

[21] Appl. No.: 286,074

[22] Filed: Dec. 19, 1988

[30] Foreign Application Priority Data

Dec. 18, 1987 [DE] Fed. Rep. of Germany ....... 3742945

[51] Int. Cl.$^5$ .............................................. A61B 3/02
[52] U.S. Cl. .................................. 351/224; 351/200; 351/246
[58] Field of Search ............... 351/222, 224, 226, 243, 351/200, 201, 203, 246

[56] References Cited

FOREIGN PATENT DOCUMENTS 3135383 10/1983 Fed. Rep. of Germany .

*Primary Examiner*—Paul M. Dzierzynski
*Attorney, Agent, or Firm*—Hill, Van Santen, Steadman & Simpson

[57] ABSTRACT

An apparatus and method for testing the visual field of a person is provided in which the apparatus comprises light point sources distributed over the visual field of the person being examined, an input device for accepting patient responses, and a control unit that allows the points of light to light up in logarithmically graduated intensity based on the patient responses. The person being examined inputs the answer "seen" or "not sheen" into the input means which relays such information to the control unit. The control unit responds accordingly and cycles the phase intensity of the light point sources through a measurement cycle having both an increasing intensity phase and a decreasing intensity phase thereby allowing a determination of the minimum threshold at which the patient can detect the points of light within his field of vision.

3 Claims, No Drawings

APPARATUS AND METHOD FOR TESTING VISUAL FIELD

BACKGROUND OF THE INVENTION

1. Field of the Invention

The present invention relates to an apparatus and method for testing the visual field of a person by correlating a series of patient responses with the varying illumination intensities of a series of points of light within the visual field of the patient.

2. Description of the Prior Art

Apparatus for testing the visual field of a person are known wherein the intensity of a point of light can be varied in steps. In such apparatus, due to the numerous lamp intensities required to adequately test the individual, the testing process may be long and laborious. As such, the patient may tire prematurely thereby causing inaccurate patient responses resulting in a false field of view measurement.

German patent DE No. 31 35 383 discloses such an apparatus for measuring the field of view of a patient. However, the apparatus is disadvantaged in that the minimum intensity at which the patient can see the point of light is not ascertained.

It is an object of the present invention to set forth an apparatus and method for measuring the field of vision of a patient wherein the minimum light intensity at which a patient can see a point of light is determined and wherein a relatively shorter test period than possible in the apparatus of the prior art is achieved.

SUMMARY OF THE INVENTION

An apparatus and method for testing the visual field of a person is provided in which the apparatus comprises light point sources distributed over the visual field of the person being examined, an input device for accepting patient responses, and a control unit that allows the points of light to light up in logarithmically graduated intensity based on the patient responses. As such, the person being examined inputs the answer "seen" or "not seen" into the input means which relays such information to the control unit. The control unit responds accordingly and cycles the phase intensity of the light point sources through a measurement cycle having both an increasing intensity phase and a decreasing intensity phase thereby allowing a determination of the minimum threshold at which the patient can detect the points of light within his field of vision.

DESCRIPTION OF THE PREFERRED EMBODIMENT

The present invention utilizes a series of light point sources which are placed within the field of vision of the patient. An input means is provided which allows the patient to interface to a control unit. The information accepted by the input means from the patient corresponds to whether or not the patient can see a particular light point source within his field of vision. As such, there are two primary patient input conditions: one condition corresponding to when the patient can see the point of light at a given intensity and the other condition corresponding to when the patient cannot see the light at a given intensity.

The control unit accepts the patient responses and controls the subsequent illumination of the corresponding light point source in a predetermined fashion. Specifically, the control unit increases the intensity of the light source in logarithmic steps when the patient responds with the "cannot see" condition (hereinafter all such increases shall be referred to as "increasing phase"). Similarly, the control unit decreases the intensity of the light source in logarithmic steps given a patient input corresponding to the "can see" condition (hereinafter all such decreases shall be referred to as "decreasing phase"). However, before an increase or decrease in light intensity ensues, the control unit compares the immediate patient input condition with the previously acquired input condition. If the condition has changed, the control unit reverses the illumination phase of the light point source. As such, the light intensity will enter a decreasing phase given a previously increasing phase and enter an increasing phase given a previously decreasing phase.

A complete and accurate measurement may be obtained from a measurement cycle consisting of at least one phase reversal. Further accuracy is attained by designing the control unit such that each increasing phase consists of at least two measurements.

For the purposes of the following illustrations, the term "light intensity" (I) (luminance) shall be defined as the brightness of the light point source expressed in candela per square centimeter ($cd/cm^2$). Likewise, for the purposes of the following illustrations the term "threshold" shall be defined as ten times the base 10 logarithm of the reciprocal of the intensity (I) as referred to an apparatus associated, freely definable maximum intensity Io. Thus, the threshold (S) may be expressed as follows:

$$S = 10 * -\log(I/Io).$$

Solving this equation for the intensity I, results in the following equation:

$$I = Io * 10^{-S/10}.$$

As expressed in the relevant equations, an increase in the intensity (I) results in a corresponding reduction in the threshold (S). Consequently, 0 dB, which corresponds to an intensity of Io, is the highest intensity that can be tested and correlates to the lowest sensitivity threshold (S).

In the control devices of the prior art, the difference between successive threshold steps is identical. Thus, because of the logarithmic character of the thresholds, there is a constant relationship between the successive intensities of the light point source during a given phase.

In contrast thereto, the control unit of the present invention selects intensity factor steps having corresponding threshold differences. As such, the graduation factor between successive intensity step values increases given increasing intensity steps and decreases given decreasing intensity steps. For the purposes of illustration, the following table of thresholds has been provided.

0 6 11 15 19 22 25 28 30 32 33 34 35 dB

Note that the difference between successive steps in a table decreases from 6 dB to 1 dB. However, tables with intermediate stages having 0.5 dB values are possible thereby creating more uniform transitions. As such, it should be noted that the above-cited table is for illustrative purposes only and is provided so that the basic principles of the invention may be set forth.

Likewise, for illustrative purposes, the threshold graduation of successive thresholds during measurement in the first phase should amount to two steps in the above-cited table. In the second phase, the graduation should amount to one step. For instance, the following measurement sequence may result given the above-cited table:

25 dB (+), 30 (+), 33 (−) // 32 (−), 30 (+) // where
(+)="can see" condition
(−)="cannot see" condition
//=intensity phase reversal.

A minimum threshold at which the patient can detect the light point source can be determined by interpolating the results of the complete measurement cycle. As such, an interpolation of the present cycle yields a threshold value of 31 dB. Similarly, a threshold value of 8.5 dB would result from the following measurement cycle:

25 dB (−), 19 (−), 11 (−), 0 (+) // 6 (+), 11 (−) //.

In the event that an input error occurs, the accuracy of the result may be severely denigrated. For instance, if the response to 19 dB in the second example set forth above was incorrectly answered with a "can see" condition (+), the following measurement cycle would result:

25 dB (−), 19 (+) // 22 (−) // thereby yielding the erroneous threshold of 20.5 dB.

To substantially limit the effects of erroneous inputs, the control unit may be designed such that the increasing phase of every measurement cycle consists of at least two measurements irrespective of a change in the patient response. Given such a design, the following measurement would result from the erroneous answer to the 19 dB threshold:

25 dB (−), 19 (+) // 22 (−), 19 (−), 15 (−), 11 (−), 6 (+) // thereby resulting in the correct threshold value of 8.5 dB.

By designing the control unit such that the graduation factor between successive intensities increases given increasing intensity and decreases given decreasing intensity, the threshold may be ascertained using a fewer number of measurements without significantly impairing the precision of the resulting minimum detectable threshold measurement. Consequently, an accurate measurement of the field of vision of the patient may be obtained with fewer individual intensity measurements.

The control unit may also be provided with an abort means to allow a premature termination of the examination after every measurement phase thereby enabling a determination of the minimum threshold detectable by the patient at the conclusion of the most recently completed phase. Although the precision of the minimum detectable threshold is reduced as a result of the premature termination, the resulting errors may be tolerable in many instances.

Although modifications and changes may be suggested by those skilled in the art, it is the intention of the inventor to embody within the patent warranted hereon any changes and modifications as reasonably and properly come within the scope of this contribution to the art.

I claim:

1. A method for testing the visual field of a person comprising the steps of:
    illuminating points of light distributed over the visual field of the person being tested at predetermined intensities;
    accepting responsive inputs from said person under test indicative of whether said person under test can see each of said points of light at said predetermined intensity;
    monitoring the intensity of each point of light;
    collecting data measurements by correlating the intensity of each point of light with a corresponding responsive input;
    increasing the intensity of a point of light when said corresponding responsive input indicates that person under test cannot see said point of light;
    decreasing the intensity of a point of light when said corresponding responsive input indicates that said person under test can see said point of light;
    changing into a next phase of reversed intensity changes when a change in said corresponding responsive input to the previous input is detected whereby the step between the logarithm of successive intensities of said point of light is increased within a phase if the phase corresponds to an increasing intensity phase and decreased within a phase if the phase corresponds to a decreasing intensity phase;
    cycling each of said points of light through a complete measurement cycle having at least one phase; and
    using the data measurements obtained during said measurement cycle to measure the field of vision of said person under test.

2. A method for testing the visual field of a person as recited in claim 1 further defined in that each measurement phase of each point of light consists of at least two data measurements regardless of a change in the corresponding responsive input.

3. A method for testing the visual field of a person as recited in claim 1 further comprising the step of accepting an abort signal thereby allowing the premature termination of the test after the completion of every phase.

* * * * *